(12) United States Patent
Venugopalan

(10) Patent No.: US 8,790,261 B2
(45) Date of Patent: Jul. 29, 2014

(54) MANUAL ULTRASOUND POWER CONTROL TO MONITOR FETAL HEART RATE DEPENDING ON THE SIZE OF THE PATIENT

(75) Inventor: Vijith Venugopalan, Karnataka (IN)

(73) Assignee: General Electric Company, Schenectady, NY (US)

(*) Notice: Subject to any disclaimer, the term of this patent is extended or adjusted under 35 U.S.C. 154(b) by 1253 days.

(21) Appl. No.: 12/644,089

(22) Filed: Dec. 22, 2009

(65) Prior Publication Data

US 2011/0152688 A1    Jun. 23, 2011

(51) Int. Cl.
| | | |
|---|---|---|
| A61B 8/00 | (2006.01) | |
| A61B 5/024 | (2006.01) | |
| A61B 5/00 | (2006.01) | |
| A61B 8/08 | (2006.01) | |
| A61B 8/02 | (2006.01) | |

(52) U.S. Cl.
CPC ......... *A61B 5/02411* (2013.01); *A61B 8/4472* (2013.01); *A61B 5/4362* (2013.01); *A61B 8/54* (2013.01); *A61B 8/0866* (2013.01); *A61B 8/02* (2013.01); *A61B 8/0883* (2013.01); *A61B 8/488* (2013.01); *A61B 8/08* (2013.01); *A61B 8/467* (2013.01); *A61B 8/4209* (2013.01)
USPC ........... 600/437; 600/439; 600/441; 600/443; 600/407

(58) Field of Classification Search
USPC .......................... 600/437, 439, 441, 407, 443
See application file for complete search history.

(56) References Cited

U.S. PATENT DOCUMENTS

| | | | |
|---|---|---|---|
| 5,257,627 A * | 11/1993 | Rapoport | 600/437 |
| 5,265,613 A * | 11/1993 | Feldman et al. | 600/453 |
| 5,413,550 A | 5/1995 | Castel | |
| 6,454,716 B1 | 9/2002 | Zumeris | |
| 7,470,232 B2 | 12/2008 | Hoctor et al. | |
| 2003/0105398 A1 | 6/2003 | Vitek | |
| 2004/0158148 A1* | 8/2004 | Amemiya | 600/437 |
| 2008/0161689 A1* | 7/2008 | Pandit | 600/438 |

* cited by examiner

*Primary Examiner* — Unsu Jung
*Assistant Examiner* — Joel Lamprecht
(74) *Attorney, Agent, or Firm* — Andrus Intellectual Property Law, LLP

(57) ABSTRACT

A continuous, noninvasive fetal heart rate measurement is produced using one or more ultrasonic transducer adhered to the abdomen of the mother. Each ultrasound transducer generates an ultrasound beam having a signal strength. The signal strength is determined by an excitation voltage applied to the ultrasound transducer. An excitation voltage adjustment device is positioned between an excitation voltage generator and the ultrasound transducer to selectively control the strength of the ultrasound beam. A user input device allows an operator to control the ultrasound signal strength to vary the depth of viewing of the fetal heart rate monitor.

21 Claims, 3 Drawing Sheets

MANUAL ULTRASOUND POWER CONTROL TO MONITOR FETAL HEART RATE DEPENDING ON THE SIZE OF THE PATIENT

BACKGROUND OF THE INVENTION

The present disclosure generally relates to methods and apparatus for determining the heart rate of a subject. More specifically, the present disclosure particularly relates to a method and apparatus for determining the beat-to-beat heart rate of a fetus.

Fetal monitoring (i.e., monitoring of the fetal condition during gestation and at birth) usually comprises monitoring uterine activity and the fetal beat-to-beat heart rate. The fetal heart rate, which provides an indication of whether the fetus is sufficiently supplied with oxygen, is preferably calculated from beat to beat.

To obtain a signal indicative of the fetal heart rate prior to rupture of the membranes, a noninvasive monitoring technique must be used. The most widely adopted measurement technique involves measuring the Doppler shift of an ultrasound signal reflected by the moving fetal heart.

In accordance with a known ultrasonic detection technique, an ultrasound transducer is placed externally on the pregnant woman's abdomen and oriented such that the transmitted ultrasound waves impinge upon the fetal heart. The reflected ultrasound waves are received either by the same or by a different ultrasound transducer. The Doppler shift of the reflected ultrasound wave is directly related to the speed of the moving parts of the heart, e.g., the heart valves and the heart walls.

Although the Doppler ultrasound is widely accepted and generally accepted method of monitoring fetal heart rate, ultrasound fetal heart rate monitoring has several drawbacks. One of these drawbacks is that the ultrasound fetal monitor transducer may not be able to monitor the fetal heart rate of a fetus in the case of an obese mother since the distance from the mother's skin surface to the fetal heart may be greater than the monitoring depth of the fetal heart rate monitor. Alternatively, ultrasonic fetal heart rate monitors that use a higher dose of ultrasound energy to increase the depth of sensing expose normal or underweight patients to a higher degree of ultrasonic energy than may be otherwise required.

BRIEF DESCRIPTION OF THE INVENTION

The present disclosure relates to a method and apparatus for determining the beat-to-beat heart rate of a fetus. In a disclosed embodiment, the continuous, non-invasive fetal heart rate measurement is produced using one or more ultrasonic transducers that are adhered or attached to the abdomen of a pregnant patient. Each ultrasound transducer generates an ultrasound beam that is reflected by the fetal heart and received by one or more of the ultrasound transducers. Based upon the received signal, the fetal heart rate monitor generates the heart rate of the fetus.

The fetal heart rate monitor of the present disclosure includes an excitation voltage generator that generates a standard excitation voltage. The excitation voltage from the excitation voltage generator is received by an excitation voltage adjustment device. The excitation voltage adjustment device, in turn, is connected to a controller that is operable to control the operation of the excitation voltage adjustment device.

During operation of the fetal heart rate monitor, an excitation voltage is initially applied to the ultrasound transducer. The signal strength of the ultrasound beam from each of the transducers is directly related to the excitation voltage.

If the strength of the ultrasound beam is insufficient to detect the fetal heart rate, a user can operate a user input device to indicate that the strength of the ultrasound beam needs to be increased. When the controller of the fetal heart rate monitor receives such a signal from the input device, the controller provides a signal to the excitation voltage device to increase the excitation voltage.

When the excitation voltage is increased by the excitation voltage adjustment device, the strength of the ultrasound beam from the ultrasound transducers increases, thereby increasing the depth of viewing for the fetal heart rate monitor. The controller operates a power level display to graphically illustrate to the operator the current signal strength from the ultrasound transducers relative to a maximum level.

The user can continue to increase the signal strength of the ultrasound beam until the fetal heart rate is detected. Once the fetal heart rate is detected, the heart rate is displayed and the user can allow the signal strength to remain at the current level. In this manner, the signal strength of the ultrasound beam is optimized for each individual patient such that each patient receives only the required ultrasound level needed to detect the fetal heart rate.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the Figures.

DETAILED DESCRIPTION OF THE INVENTION

Figure 1:
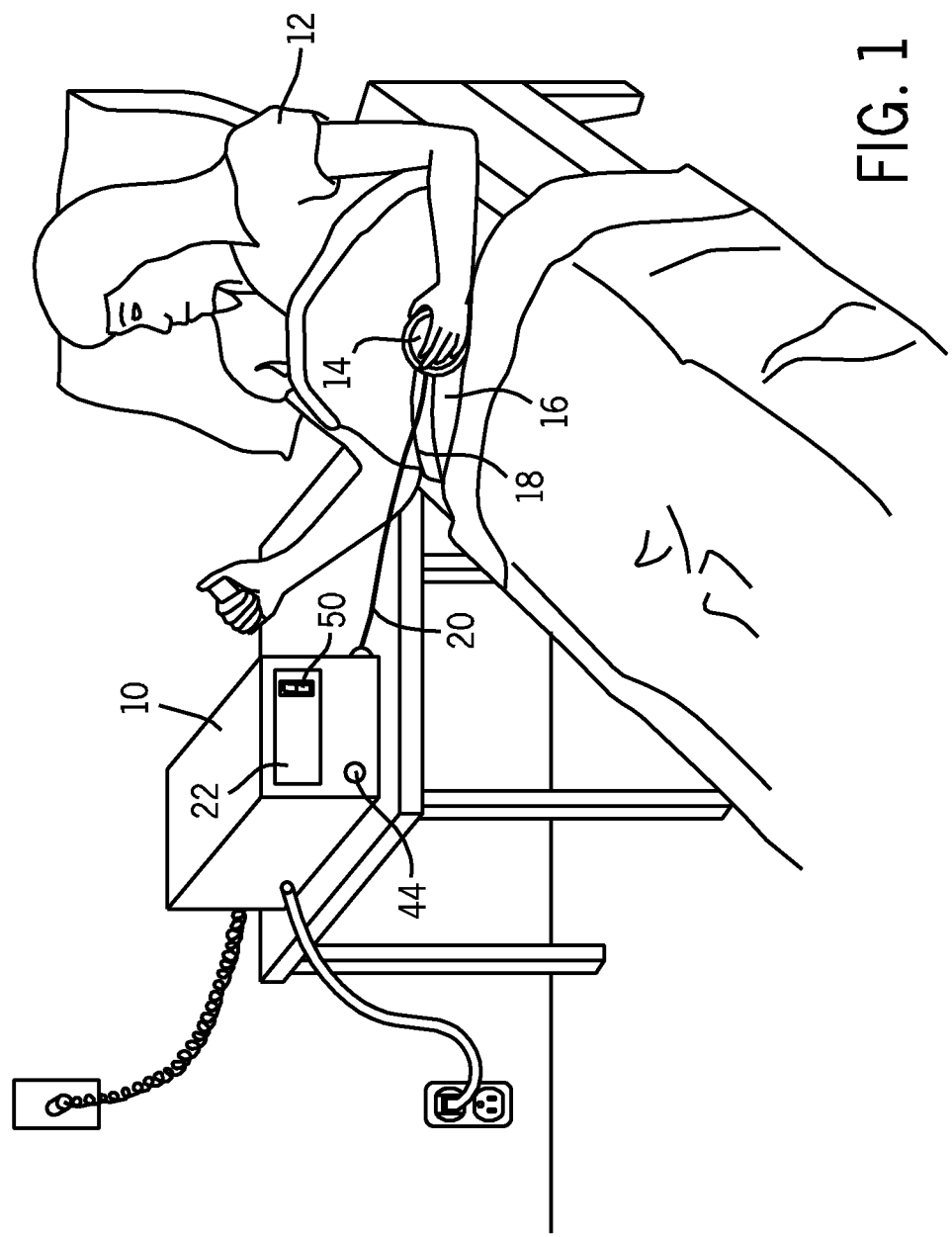
FIG. 1 depicts a pregnant patient utilizing fetal heart rate monitor.

FIG. 1 illustrates a fetal heart rate monitor 10 that can be used to monitor the heart rate of the fetus of a pregnant patient 12. Although the fetal heart rate monitor 10 is shown in FIG. 1 in one exemplary form, it should be understood that the fetal heart rate monitor 10 could take many other forms while operating within the scope of the present disclosure.

In the embodiment of FIG. 1, the fetal heart rate monitor 10 includes an ultrasound probe 14 that is secured to the patient's abdomen 16 by a strap 18. The ultrasound probe 14 is shown in the embodiment of FIG. 1 as being coupled to the fetal heart rate monitor 10 by cable 20. However, it is contemplated that the fetal heart rate monitor 10 could communicate with the ultrasound probe 14 using a wireless communication technique.

The fetal heart rate monitor 10 is shown in FIG. 1 as including a display screen 22 that typically displays the monitored heart rate of the fetus. The display screen 22 can be configured to display other monitored signals obtained from the patient 12.

During operation, when the fetal heart rate monitor 10 is powered on, one or more ultrasound transducers contained within the ultrasound probe 14 each generate an ultrasound beam directed into the patient 12 through the skin of the abdomen. The fetal heart rate monitor 10 monitors the ultrasound signal returned to either the same or a different ultrasound transducer contained within the ultrasound probe 14 to detect the beating of the fetal heart. Based upon data acquired from the ultrasound probe 14, the fetal heart rate monitor 10 calculates the fetal heart rate and displays the calculated fetal heart rate on the display 22 in a known manner.

Figure 2:
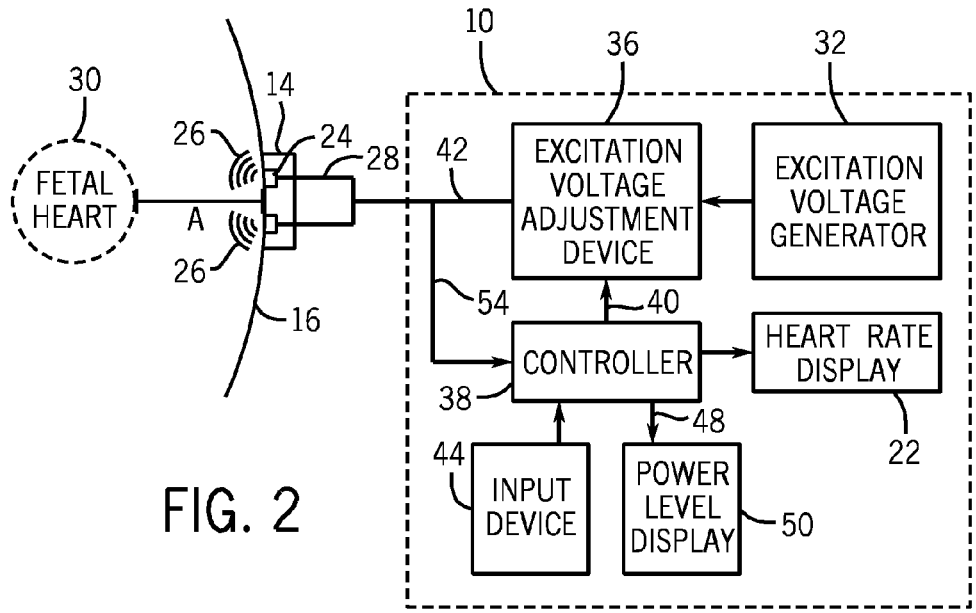
FIG. 2 is a schematic illustration of the ultrasound power control system of the present disclosure.

Referring now to FIG. 2, the detailed operation of the fetal heart rate monitor 10 will now be described. As illustrated in FIG. 2, the ultrasound probe 14 is positioned on the exterior surface of the patient's abdomen 16. In the embodiment shown in FIG. 2, the ultrasound probe 14 includes multiple ultrasound transducers 24. Each transducer 24 is operable to both generate an ultrasound beam 26 and receive reflected ultrasound energy from the fetal heart. In one embodiment of the disclosure, each of the ultrasound transducers 24 is a piezoelectric crystal that vibrates to create the ultrasound beam 26 emanating from the ultrasound transducer. The vibration of the piezoelectric crystal is created by an excitation voltage applied to the piezoelectric crystal through a voltage supply line 28.

Although in the embodiment shown in FIG. 2 each of the ultrasound transducers 24 is able to both transmit the ultrasound beam and receive the reflected ultrasound energy, the ultrasound probe 14 could utilize separate transducers for transmitting and receiving the ultrasound energy.

During operation of the fetal heart rate monitor 10, the ultrasound transducers 24 generate the ultrasound beam 26 that penetrates the patient's abdomen 16 and travels into the pregnant patient until the ultrasound signal is reflected by the beating fetal heart 30. As illustrated in FIG. 2, the distance A from the outer surface of the abdomen 16 to the fetal heart 30 must fall within the range of detection for the ultrasound transducers 24. The range of detection of the ultrasound transducers 24 is directly related to the signal strength of the ultrasound beam 26. In turn, the strength of the ultrasound beam 26 is directly related to the voltage level of the excitation voltage applied to the ultrasound transducers 24 along the voltage supply line 28. If the position of the fetal heart 30 is outside of the detection range of the ultrasound transducers 24, the fetal heart rate monitor 10 is unable to detect the heart rate of the fetus. In currently available fetal heart rate monitors, the value of the excitation voltage is selected such that the sensing distance of the ultrasound probe is sufficient to detect the fetal heart rate in a normal pregnant patient.

When the fetal heart rate monitor 10 is used with an obese patient, the distance A from the patient's abdomen 16 to the fetal heart 30 can be much greater than with a relatively thin or normal patient.

Referring now to FIG. 2, the fetal heart rate monitor 10 of the present disclosure includes circuitry that allows the power output, and thus the monitoring depth, of the ultrasound probe 14 to be selectively modified by a user. The selective modification of the power output of the ultrasound probe 14 allows the ultrasound probe 14 to detect the fetal heart rate at varying distances from the patient's abdomen 16. Further, the fetal heart rate monitor 10 of the present disclosure allows an operator to control the amount of ultrasound power delivered to the pregnant patient.

As illustrated in FIG. 2, the fetal heart rate monitor 10 includes an ultrasound excitation voltage generator 32. The excitation voltage generator 32 generates the typical excitation voltage that is used to drive the piezoelectric crystals that are incorporated into the ultrasound transducer 24. The excitation voltage is sinusoidal voltage that is generated along voltage line 34. In prior fetal heart rate monitoring systems, the excitation voltage along voltage line 34 is applied directly to the ultrasound transducers 24. In such a prior art system, the excitation voltage level is fixed and cannot be modified by the user of the fetal heart rate monitor.

In the embodiment shown in FIG. 2, an excitation voltage adjustment device 36 is positioned between the excitation voltage generator 32 and the ultrasound transducers 24. The excitation voltage adjustment device 36 receives the excitation voltage along line 34 and is operable to selectively amplify or reduce the excitation voltage as desired. The excitation voltage adjustment device 36 receives a voltage adjustment control signal from a controller 38 along a control line 40. In the embodiment illustrated, the controller 38 generates a control signal along line 40 that controls the voltage adjustment device 36 to selectively increase or decrease the excitation voltage from the excitation voltage generator 32. The modified excitation voltage from the voltage adjustment device 36 is provided to the ultrasound transducer 24 along the voltage supply line 42.

In the embodiment of the disclosure shown in FIG. 2, the controller 38 is a microprocessor that can generate digital signals along the control line 40 to the excitation voltage adjustment device 36. Although the controller 38 is shown as a microprocessor, the controller 38 could be a microcontroller, FPGA and CPLD while operating within the scope of the disclosure. In the embodiment of FIG. 2, a user input device 44 is coupled to the controller 38 such that a user, such as a clinician, can control the modification of the excitation voltage by the excitation voltage adjustment device 36. In one embodiment of the disclosure, the input device 44 is a track ball. The controller 38 senses the movement of the track ball that forms the input device 44 and generates a control signal to the excitation voltage adjustment device 36 to either increase or decrease the excitation voltage. Although the input device 44 is contemplated as being a track ball, the input device 44 could take various other forms while operating within the scope of the present disclosure. As an example, the input device 44 could be an adjustable dial slide switch or a touch screen incorporated as part of the display screen for the fetal heart rate monitor 10.

As discussed previously, the value of the excitation voltage directly impacts the signal strength of the ultrasound beam 26. Thus, if the strength of the ultrasound beams 26 needs to be increased to increase the depth of viewing, the operator moves the input device 44 in the direction to increase the ultrasound signal strength. The controller 38 provides a control signal along line 40 to the excitation voltage adjustment device 36 to increase the excitation voltage. The user can continue to increase the strength of the excitation voltage until the fetal heart rate is detected and displayed on the heart rate display 22. Once the fetal heart rate has been detected, the clinician can discontinue the increase in the excitation voltage, and thus the ultrasound signal strength. In this manner, the clinician, through the fetal heart rate monitor 10, utilizes only the required ultrasound signal required to detect the fetal heart rate.

Figure 5:
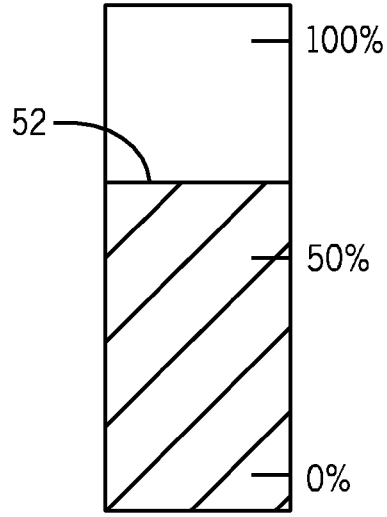
FIG. 5 is a graphic display of the power level of the ultrasound beam.

As the input device 44 is activated to increase the signal strength of the ultrasound beam, the controller 38 can generate a feedback signal along line 48 to a power level display 50. The power level display 50 allows the user to visually determine the signal strength of the ultrasound beam on a visual display. FIG. 5 illustrates the power level display 50 in accordance with one embodiment. In the embodiment of FIG. 5, the power level display 50 is a bar having demarcations between 0 and 100% of the signal strength. A moving indicator line 52 indicates the current signal strength.

Although the power level display 50 and the heart rate display 22 are shown separate in FIG. 2, it should be understood that the two displays could be shown on the same display screen, as is illustrated in FIG. 1. Further, in the embodiment illustrated in FIG. 1, the input device 44 is shown as being incorporated directly into the heart rate monitor 10. Additionally, the controller 38 shown in FIG. 2 as controlling the excitation voltage adjustment device 36 could either be separate or integrated into the controller or the entire fetal heart rate monitor 10.

Referring back to FIG. 2, the controller 38 can preferably include a feedback line 54 such that the controller 38 can monitor the modified excitation voltage present on the voltage supply line 42. Through the feedback line 54, the controller can monitor the modified excitation voltage and limit the maximum value of the excitation voltage supplied to the ultrasound transducers 24. In this manner, the controller 38 can limit the maximum strength of the ultrasound signal supplied to the pregnant patient.

Figure 3:
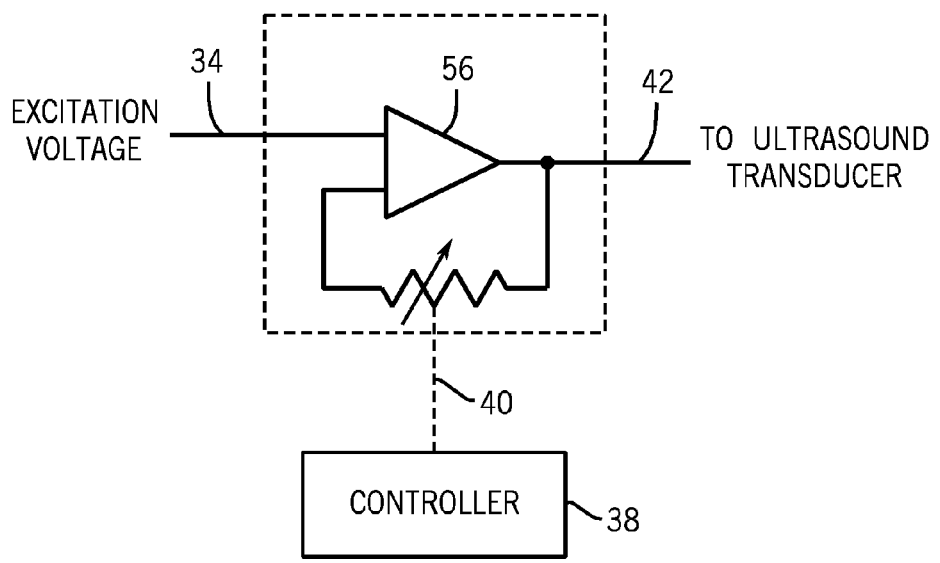
FIG. 3 is one embodiment of the excitation voltage adjustment device.

Referring now to FIG. 3, a first embodiment of the excitation voltage adjustment device 36 is illustrated. In this embodiment, the excitation voltage present along line 34 is lower than a desired value to be fed to the ultrasound transducers. In the voltage adjustment device 36 shown in FIG. 3, an amplifier 56 receives the excitation voltage from line 34 and amplifies the voltage, which is then output along the voltage supply line 42. In the simplified embodiment shown in FIG. 3, a variable resistor 58 is connected to the controller 38. The controller 38 can adjust the value of the resistor 58 to control the gain of the amplifier 56. It should be understood that the embodiment shown in FIG. 3 is a schematic illustration only and could take many different forms while operating within the scope of the present disclosure. However, the embodiment of FIG. 3 illustrates that the excitation voltage adjustment device 36 could be an amplification circuit that amplifies the excitation voltage on line 34 to generate the modified excitation voltage along the voltage supply line 42.

Figure 4:
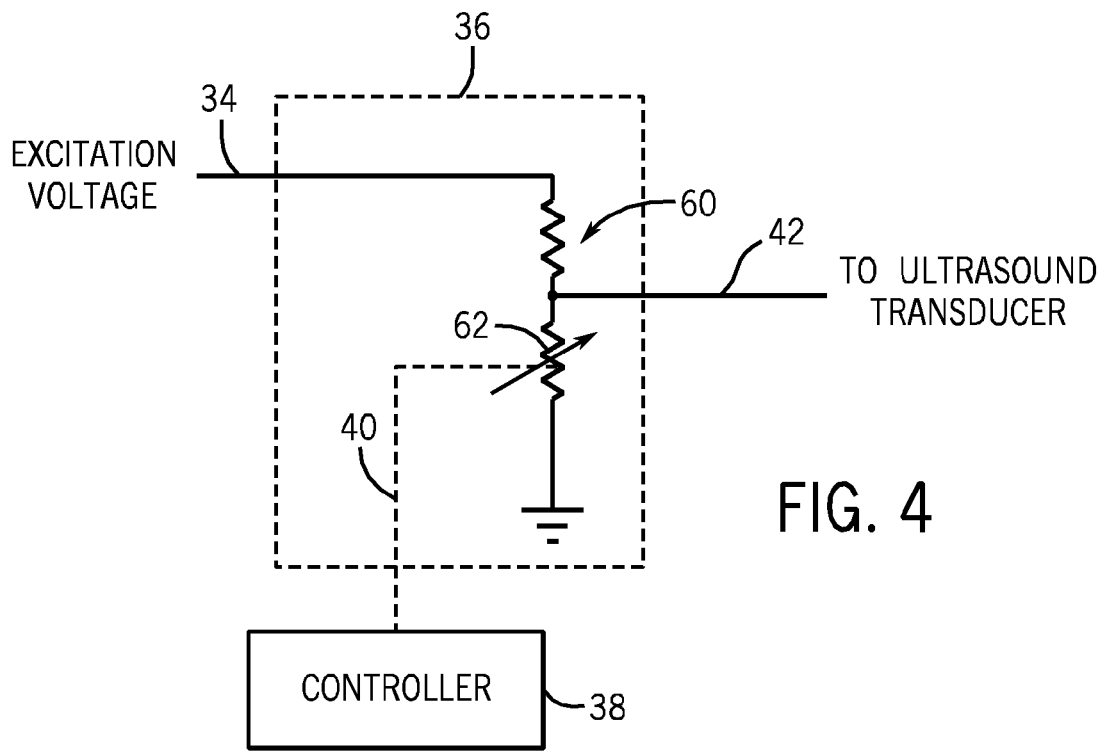
FIG. 4 is a second embodiment of the excitation voltage adjustment device.

Referring now to FIG. 4, an alternate embodiment of the voltage adjustment device 36 is illustrated. In this embodiment, the excitation voltage along line 34 is fed into a voltage reduction circuit 60. The voltage reduction circuit 60 is a voltage divider including a variable resistor 62 that forms one-half of a simple voltage divider. The variable resistor 62 is coupled to the controller 38 through the control line 40. The controller 38 is able to control the value of the resistor 62 to modify the excitation voltage that is present along the voltage supply line 42. Once again, the circuitry of the embodiment shown in FIG. 4 is simplified for illustrative purposes only. However, it should be understood that the voltage adjustment device 36 shown in FIG. 4 reduces the excitation voltage from an elevated value to the desired value supplied to the ultrasound transducer.

In an alternate embodiment of the disclosure, the controller 38 can monitor the ultrasound signal received from the ultrasound probe 14 and provide a control signal along line 40 to the excitation voltage adjustment device 36 to either increase or decrease the excitation voltage based upon the received signal. In such an example, the controller 38 determines the strength of the ultrasound signal received and, if the signal strength is below a predetermined threshold, the controller 38 increases the excitation voltage. This process continues until the received ultrasound signal reaches the predetermined threshold. Likewise, if the ultrasound signal received from the probe 14 exceeds the predetermined threshold, the controller 38 can automatically decrease the excitation voltage until the received signal drops to the predetermined threshold. In such a manner, the controller 38 can automatically control the excitation voltage based upon a feedback signal received from the probe 14. It is contemplated that the fetal heart rate monitor 10 could include some type of input device that allows the monitor to toggle between either a manual mode or a servo mode depending upon specific requirements from the operator.

As can be understood by the previous description, the fetal heart rate monitor 10 of the present disclosure allows an operator to adjust the signal strength of the ultrasound beams such that only the required dose of ultrasound energy is supplied to the patient to detect the fetal heart rate. When the fetal heart rate monitor 10 is utilized with a small, underweight patient, the signal strength can be significantly reduced. Likewise, when the fetal heart rate monitor is utilized with an obese patient, the signal strength can be greatly increased to increase the depth of viewing to detect the fetal heart rate. In this manner, the fetal heart rate monitor 10 of the present disclosure can be utilized with a larger variety of pregnant patients as compared to currently available devices.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. An apparatus for determining the heart rate of a ferns, comprising:
   at least one ultrasound transducer operable to generate an ultrasound beam and receive a reflected ultrasound signal, the generated ultrasound beam having a signal strength;
   a controller coupled to the ultrasound transducer to receive the reflected ultrasound signal and determine the heart rate of the fetus;
   an excitation voltage generator operable to supply an excitation voltage to the ultrasound transducer; and
   an excitation voltage adjustment device positioned between the excitation voltage generator and the ultrasound transducer, wherein the excitation voltage adjustment device is operable to modify the excitation voltage supplied to the ultrasound transducer, wherein the signal strength of the ultrasound beam is related to the excitation voltage.

2. The apparatus of claim 1 wherein the controller is coupled to the excitation voltage adjustment device, the controller being operable to control the excitation voltage adjustment device to modify the excitation voltage.

3. The apparatus of claim 2 further comprising a manual input device coupled to the controller, wherein the manual input device allows a user to selectively modify the excitation voltage.

4. The apparatus of claim 2 further comprising a power level display coupled to the controller, wherein the signal strength of the ultrasound beam is displayed on the power level display.

5. The apparatus of claim 3 wherein the manual input device is a track ball.

6. The apparatus of claim 1 wherein the excitation voltage adjustment device includes an amplifier operable to selectively amplify the excitation voltage from the excitation voltage generator.

7. The apparatus of claim 1 wherein the excitation voltage adjustment device includes a voltage divider operable to selectively reduce the excitation voltage received from the excitation voltage generator.

8. A method of monitoring a fetal heart rate, comprising:
positioning at least one ultrasound transducer on an abdomen of a pregnant patient;
operating an excitation voltage generator to supply an excitation voltage;
receiving the excitation voltage at an excitation voltage adjustment device, wherein the excitation voltage device is positioned between the excitation voltage generator and the ultrasound transducer;
modifying the operational characteristics of the excitation voltage adjustment device to selectively modify the excitation voltage;
supplying the modified excitation voltage to the ultrasound transducer, wherein the ultrasound transducer creates an ultrasound beam having a signal strength related to the modified excitation voltage; and
receiving a reflected ultrasound signal in a controller, wherein the controller determines the fetal heart rate based on the reflected ultrasound signal.

9. The method of claim 8 further comprising the step of generating a control signal from the controller coupled to the excitation voltage adjustment device to modify the excitation voltage.

10. The method of claim 9 wherein the controller receives a manual input signal from an input device coupled to the controller.

11. The method of claim 9 further comprising the step of displaying the signal strength of the ultrasound beam.

12. The method of claim 11 wherein the signal strength is displayed as the excitation voltage is modified by the user.

13. The method of claim 12 wherein the signal strength is displayed relative to a maximum signal strength.

14. The method of claim 9 wherein the controller limits excitation voltage to keep the signal strength of the ultrasound beam below a maximum.

15. The method of claim 8 wherein the excitation voltage adjustment device operates to selectively reduce the excitation voltage.

16. The method of claim 8 wherein the excitation voltage adjustment device operates to selectively amplify the excitation voltage.

17. The method of claim 9 wherein the controller receives the reflected ultrasound beam from the ultrasound transducer and automatically adjusts the excitation voltage based on the received ultrasound signal.

18. A method of monitoring a fetal heart rate, comprising;
positioning at least one ultrasound transducer on an abdomen of a pregnant patient;
operating an excitation voltage generator to supply an excitation voltage;
receiving the excitation voltage at an excitation voltage adjustment device, wherein the excitation voltage device is positioned between the excitation voltage generator and the ultrasound transducer;
positioning a controller in communication with the excitation voltage adjustment device, wherein the controller is operable to modify operational characteristics of the excitation voltage adjustment device to selectively modify the excitation voltage;
receiving a user input at the controller, the user input indicating a desired signal strength for an ultrasound beam from the ultrasound transducer;
operating the controller to modify the excitation voltage received by the excitation voltage adjustment device;
supplying the modified excitation voltage to the ultrasound transducer such that the ultrasound transducer creates the ultrasound beam having the desired signal strength;
receiving a reflected ultrasound signal in a controller, wherein the controller determines the fetal wart rate based on the reflected ultrasound signal; and
displaying the signal strength of the ultrasound beam and the fetal heart rate.

19. The method of claim 18 wherein the controller receives the manual input signal from the user through an input device coupled to the controller.

20. The method of claim 18 wherein the excitation voltage adjustment device operates to selectively reduce the excitation voltage from the excitation voltage generator.

21. The method of claim 18 wherein the excitation voltage adjustment device operates to selectively amplify the excitation voltage from the excitation voltage generator.

* * * * *